US006871998B2

(12) United States Patent
Carter et al.

(10) Patent No.: US 6,871,998 B2
(45) Date of Patent: Mar. 29, 2005

(54) METHOD FOR CALIBRATING A VACUUM THERMOGRAVIMETRIC ANALYZER FOR DETERMINATION OF VAPOR PRESSURES OF COMPOUNDS

(75) Inventors: Malika Dothresa Carter, San Jose, CA (US); Michael Andrew Parker, Fremont, CA (US)

(73) Assignee: Hitachi Global Storage Technologies Netherlands B.V., Amsterdam (NL)

( * ) Notice: Subject to any disclaimer, the term of this patent is extended or adjusted under 35 U.S.C. 154(b) by 0 days.

(21) Appl. No.: 10/632,507

(22) Filed: Aug. 1, 2003

(65) Prior Publication Data

US 2005/0025214 A1 Feb. 3, 2005

(51) Int. Cl.$^7$ ............................. G01N 25/20; G01N 5/04
(52) U.S. Cl. ............................. 374/14; 374/1; 374/176; 252/408.1; 252/62.55; 252/962; 324/203
(58) Field of Search ............................. 374/14, 12, 2, 374/1, 176; 324/203; 252/408.1, 62.51 R, 62.55, 962

(56) References Cited

U.S. PATENT DOCUMENTS

| | | | | |
|---|---|---|---|---|
| 3,413,540 A | * | 11/1968 | Vansant | 374/176 |
| 3,554,001 A | | 1/1971 | Norem | 374/14 |
| 3,850,706 A | * | 11/1974 | Street | 252/62.55 |
| 3,902,354 A | | 9/1975 | Harlan et al. | 374/14 |
| 4,208,911 A | * | 6/1980 | Tchernev | 374/176 |
| 4,246,641 A | * | 1/1981 | Babil et al. | 374/1 |
| 4,537,517 A | * | 8/1985 | Inomata et al. | 374/21 |
| 4,824,790 A | | 4/1989 | Carangelo et al. | 436/157 |
| 5,294,553 A | | 3/1994 | Kawahara | 436/60 |
| 5,346,306 A | | 9/1994 | Reading et al. | 374/10 |
| 5,703,342 A | * | 12/1997 | Hoffmann et al. | 374/1 |
| 5,775,810 A | * | 7/1998 | Shin | 374/176 |
| 6,354,732 B1 | * | 3/2002 | Casati et al. | 374/14 |

FOREIGN PATENT DOCUMENTS

JP          04120440 A  *  4/1992  ............ G01N/5/04

OTHER PUBLICATIONS

ASTM E1582–00, "Standard Practice for Calibration of Temperature Scale for Thermogravimetry," ASTM, Committee: E37.01 (Published Apr. 2001), 9 pages.*

ISO 11358:1997(E), "Plastics—Thermogravimetry (TG) of polymers—General principles," Committee: ISO TC 61/SC 5 (Published Apr. 1997), 10 pages.*

(Continued)

*Primary Examiner*—Christopher W. Fulton
*Assistant Examiner*—Stanley J. Pruchnic, Jr.
(74) *Attorney, Agent, or Firm*—Lewis L. Nunnelley

(57) ABSTRACT

The invention provides a method for accurately calibrating a vacuum thermogravimetric analyzer (VTGA). The invention solves the problem of calibrating a VTGA by using the actual magnetic transitions and associated transition temperatures, or Curie temperatures, $T_c$'s, of a set of standards which can be used in-situ at the location of the sample holder obviating the difficulties associated with indirect methods of calibration. The invention encompasses a method of using a set of calibration standards comprised of a plurality of ferromagnetic slugs to provide a temperature calibration for a VTGA. The method permits accurate calibration through sufficiently numerous calibration points over a rather limited low-temperature range for determining vapor pressures of compounds. Through the use of these standards, highly accurate measurements can be made of the vapor pressures of critical hard disk drive compounds, such as lubricants, and corrosion inhibitors, that are crucial to competitive disk drive technology.

1 Claim, 5 Drawing Sheets

OTHER PUBLICATIONS

Norem, S. D.; O'Neill, M. J.; Gray, Allan P.; "Use of magnetic transitions in temperature calibration and performance evaluation of thermogravimetric systems," Thermochimica Acta (1970), 1(1), 29–38.* www.ssi.shimadzu.com/service/pdfs/tga_call.pdf "standard cleaning and calibration procedure for TGA–50 Certified Curie Point standards" (SRM–71 N1st) p. 1–9 (no date).

ASTM–Summary Practice E1582–93– "Standard Practice for Calibration of Temperature Scale for Thermogravimetry" (Publ. Jan. 1994) (1 page).

Kelsey and Truttmann; "Complete Thermogravimetric Analysis" May 1997 pp. 16, 18, 20, 22.

http://www.n/ci.com/users/gundlach/calib_stand.html; Curie Point Standards For TGA Calibration. (8 pages, Mar. 2001).

* cited by examiner

METHOD FOR CALIBRATING A VACUUM THERMOGRAVIMETRIC ANALYZER FOR DETERMINATION OF VAPOR PRESSURES OF COMPOUNDS

RELATED APPLICATION

Applicant's application entitled "STANDARDS FOR THE CALIBRATION OF A VACUUM THERMOGRAVIMETRIC ANALYZER FOR DETERMINATION OF VAPOR PRESSURES OF COMPOUNDS" (Ser. No. 10/632,650) and commonly assigned was filed simultaneously with the present application and contains related subject matter.

BACKGROUND OF THE INVENTION

1. Field of the Invention

The present invention relates to methods for determining the amounts of corrosion inhibitor and lubricant to be used in hard disk drives from measurements of the vapor pressure of such constituents. More specifically, the invention relates to a method for measuring vapor pressures of such compounds using a vacuum thermogravimetric analyzer (VTGA), and particularly to a method of accurately calibrating the temperature of the VTGA based on a set of novel Curie temperature standards.

2 Description of the Background Art

Disk drives using magnetic recording of digital information store most of the data in contemporary computer systems. A disk drive has at least one rotating disk with discrete concentric tracks of data Each disk drive also has at least one recording head typically having separate write element and read element for writing and reading the data on the tracks.

As areal densities increase, the impetus to reduce the spacing between the active elements of the head and the disk becomes stronger. Since it is becoming increasingly difficult to reduce the fly height which is a substantial portion of this spacing, it becomes desirable to make other structures that contribute to this overall spacing thinner, such as the protective overcoat layers on the head and the disk. However, as these overcoat layers become thinner, the head and the disk become more susceptible to pinhole formation in these very thin films, ~<7 nm. Such pinholes act as conduits for attack by corrosive constituents, and by wear in the head/disk enclosure. To overcome the deleterious effects of corrosion and wear of head and disk components having thinner protective overcoat layers, remedies such as corrosion inhibitors and lubricants that are transported in the vapor phase from reservoirs within the head/disk enclosure to the sites of corrosive attack and wear are being developed. However, the cost of these additional chemical remedies can be quite significant. Also, the disk drive must have sufficient amounts of these constituents present during the expected operational lifetime of the disk drive. These two factors make the determination of accurate amounts of such constituents for the charging of internal disk drive reservoirs crucial for cost competitive disk drive technology. Therefore, a critical aspect of such determinations is having accurate data on the vapor pressure of these corrosion inhibitors and lubricants under disk drive operating conditions. A thermogravimetric analyzer (TGA) can be modified to make measurements of vapor pressure. To make vapor pressure measurements, the TGA is modified to make measurements in vacuum of weight loss from compounds of interest. The small changes of weight are measured in vacuum as vapor effuses from a Knudsen cell containing the material of interest, viz. rust inhibitor, or lubricant. When this vacuum TGA, or VTGA, is used to measure vapor pressure, it is found that the expected vapor pressures of known samples deviate significantly from published values. This is probably the result of inefficient heat transfer within the test cell, sample holder, under vacuum, heat being transferred to the sample by infrared radiation, rather than more efficiently by convection or by diffusion at ambient atmospheric pressure, as is the case for non-vacuum TGAs. A variety of methods have been used in attempts to calibrate the VTGA: placing thermocouples in close proximity to the sample, welding thermocouples to the sample holder, and using calibration standards consisting of liquids with known vapor pressures. The method of placing the thermocouple in close proximity to the sample holder is inadequate, because it is difficult to reproducibly locate the thermocouple at the same position from one measurement to the next. The method of welding a thermocouple to the sample holder is less than satisfactory, because it is likewise difficult to produce the tiny weld required. The method of using liquids with known vapor pressures, while in theory is promising, in practice proves to be illusive, because small amounts of impurities significantly alter vapor pressure, and it is difficult to find or produce liquids with sufficient purity for accurate vapor pressure measurements in the temperature ranges of interest.

These problems are exacerbated because vapor pressure is a sensitive function of temperature. For accurate measurements of vapor pressure it is necessary to accurately know the temperature over which the measurement is made. Because of the problems with heat transport in vacuum associated with the VTGA, numerous temperature calibration standards are required to span the limited temperature range of interest. Moreover, the choice of a suitable calibration standard is limited. Typically a standard used for TGA calibration based on magnetic transitions at a Curie temperature is not suitable for the lower temperatures of interest for vapor pressure measurements. Because a typical standard for TGA calibration is fabricated from a pure element to avoid problems with impurities that affect the transition, elemental standards have been the standards of choice and are, therefore, limited to Ni, Fe, and Co, all of which have relatively high Curie temperatures for their magnetic transitions which are unsuitable for vapor pressure measurements at low temperature.

Accordingly one method for calibration at low temperatures suitable for vapor pressure measurements is based on the use of compounds with known vapor pressure. Obtaining vapor pressure standards is often difficult and time consuming due to the elaborate distillation procedures employed to produce vapor pressure standards of sufficient purity.

A calibration standard selected from an alloy or element with a well-known magnetic transition temperature, Curie temperatures, or Curie points, as mentioned above, also have shortcomings. Although a calibration method based on a magnetic standard is desirable, obtaining such standards is difficult. Nevertheless, the relative simplicity of a calibration method based on magnetic standards makes their use appealing. The calibration method using magnetic standards is based on the principle that a magnetic standard, when placed in an external magnetic field, produces a change in apparent weight as the standard undergoes a magnetic transition at its Curie temperature. Specifically, a known calibration method based on a magnetic standard includes: placing a magnetic standard on the balance pan, sample holder, of the TGA; placing a magnet near the standard so that a magnetic force of attraction is exerted on the standard which alters the apparent weight registered on a microbalance to which the pan is attached; as the temperature in the sample chamber is increased, the standard passes through a magnetic transition, becoming non-ferromagnetic upon heating above the Curie temperature, $T_c$; at the same time, the microbalance registers an effective change in weight associated with the loss of the magnetic force that was previously acting upon the standard below the Curie temperature.

Monel, a CuNi alloy with about 28 to 30% by weight of Cu, has been used as a single standard. This standard is of particular interest because it has a magnetic transition in the low temperature regime at about 65 C. A problem with a calibration method using the Monel standard is that it is virtually the sole standard available in the low temperature regime. However, in attempting to use an available slug of Monel to calibrate a VTGA, a problem with the stability of the standard is encountered. With the passage of time, the Monel standard loses magnetic moment and it no longer exhibits a magnetic transition.

What is needed is a method for accurately calibrating a vacuum thermogravimetric analyzer (VTGA). What is needed is a set of novel standards that free the calibration method from concerns about: placement of thermocouples in proximity to the sample, welding of thermocouples on the sample holder, or purity of vapor pressure standards. What is needed is a set of standards that permits accurate calibration through sufficiently numerous calibration points over a limited low-temperature range for determining vapor pressures of compounds of interest.

SUMMARY OF THE INVENTION

In a preferred embodiment, the invention provides a method for employing a set of Curie temperature standards to calibrate a VTGA. In one embodiment the method includes: determining the Curie temperatures, $T_c$'s, of each slug in a set of standards in a TGA; placing each slug in the sample holder of a VTGA within a magnetic field; setting a temperature of the VTGA to a temperature corresponding to a set-point temperature greater than the Curie temperature, $T_c$, of the slug by an amount equal to a first offset value; holding the temperature of the VTGA at a temperature corresponding to a set-point temperature for a first time interval sufficient to allow the VTGA to thermally equilibrate; increasing the temperature of the VTGA to a set-point temperature greater than an immediately preceding set-point by amount equal to a second offset value; holding the temperature of the VTGA at a temperature corresponding to a set-point temperature for a second time interval sufficient to allow the VTGA to thermally equilibrate; and, repeating the previous two operations, if the slug has not lost magnetization, i.e. reaching the Curie temperature, $T_c$, until the slug has lost magnetization, whereupon the set-point temperature at which the slug loses magnetization is recorded as the apparent Curie temperature of the slug. This procedure is repeated until the Curie temperatures of all slugs has been determined. In another embodiment of the calibration method of the invention, the first offset value is chosen to be about 10 degrees; the second offset value is chosen to be about 2 degrees; the VTGA is allowed to thermally equilibrate for a first time interval of about 1 hour; and, the set point temperature is increased by heating at a rate of ~5 degrees/min; whereupon the VTGA is allowed to thermally equilibrate for a second time interval of about 2 hours.

In summary, the invention provides a method for accurately calibrating a vacuum thermogravimetric analyzer (VTGA). The invention provides an accurate calibration through the use of novel standards that free the calibration method from concerns about: placement of thermocouples in proximity to the sample, welding of thermocouples on the sample holder, or purity of vapor pressure standards. The invention solves the problem of calibrating a VTGA by using the actual magnetic transitions and associated transition temperatures, or Curie temperatures, $T_c$'s, of a set of standards which can be used in-situ at the location of the sample holder obviating the difficulties associated with indirect methods of calibration. Moreover, the set of novel standards permits accurate calibration over a selected low temperature range of interest providing a set of calibration points that are sufficiently numerous to determine the vapor pressure of a compound. In addition, the invention provides a calibration based upon a plurality of such standards, whose number can be chosen to provide calibration curves with any desired accuracy over a selected range of temperatures. In this way, a VTGA is calibrated to provide highly accurate measurements of the vapor pressures of critical hard disk drive compounds, such as lubricants, and corrosion inhibitors, that are crucial to competitive disk drive technology.

Other aspects and advantages of the present invention will become apparent from the following detailed description, which, when taken in conjunction with the drawings, illustrate by way of example the principles of the invention.

DETAILED DESCRIPTION OF THE INVENTION

One embodiment of the present invention provides a novel method for calibration of a VTGA through measuring temperature at the exact location of the sample within the instrument at the sample holder.

Figure 1:
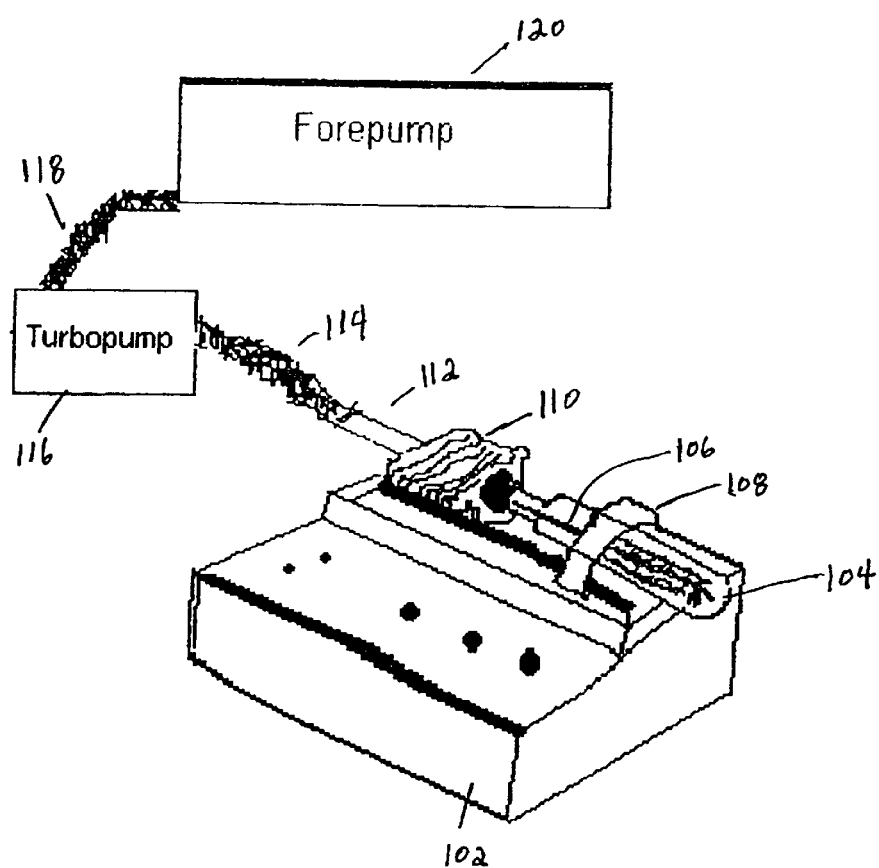
FIG. 1 illustrates a schematic diagram of a VTGA.
Figure 2:
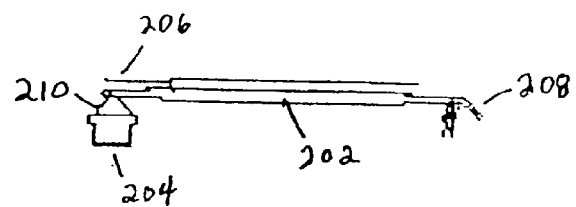
FIG. 2 illustrates a schematic diagram of a sample arm assembly with a sample holder.

FIGS. 1 and 2 are schematic diagrams showing the components of the VTGA in relation to the location of a sample in the sample holder. As illustrated in FIG. 1, the VTGA comprises: a electronic control unit, 102; a glass enclosure, 104, which envelopes a sample balance arm, 106, that is inserted into a balance assembly, 108; a furnace, 10; a large conductance evacuation tube, 112; a vacuum hose connecting the evacuation tube, 114, with a turbopump, 116; a vacuum hose connecting the turbopump, 118, with a forepump or backing pump, 120. The features differentiating the VTGA from a TGA are modifications to the TGA that permit measurements in vacuum, in particular, the attached vacuum components, 112 through 120, that allow the operator to evacuate the glass enclosure containing the sample balance arm assembly. In other respects, the VTGA is functionally very similar to a TGA; and the VTGA is operated in essentially the same manner known in the art for a TGA.

To use the VTGA, a sample is placed in the sample holder, which may be as simple as a balance pan, or for vapor pressure measurements, as complex as a Knudsen effusion cell: The sample holder is attached to the sample balance arm and both the sample holder with sample and the balance arm are inserted into the balance assembly. The balance arm and balance assembly are situated so that the sample holder is located within the furnace; the glass enclosure is used to cover the balance arm and prevents air currents from interferring with the measurements made by the balance assembly in a TGA, but provides the added function of a vacuum enclosure for a VTGA.

FIG. 2 is a schematic diagram showing the sample balance arm, 106, with sample holder attached thereto. The sample balance arm comprises: a load beam, 202; a sample holder, 204; a thermocouple, 206, in proximity to the sample holder, 204; and, a counterweight, 208. The sample holder shown in FIG. 2 is a Knudsen effusion cell which is required for one embodiment of the invention directed to calibration of the VTGA for vapor pressure measurements. The Knudsen effusion cell is shown suspended from the load beam by a Pt stirrup, 210.

Figure 3:
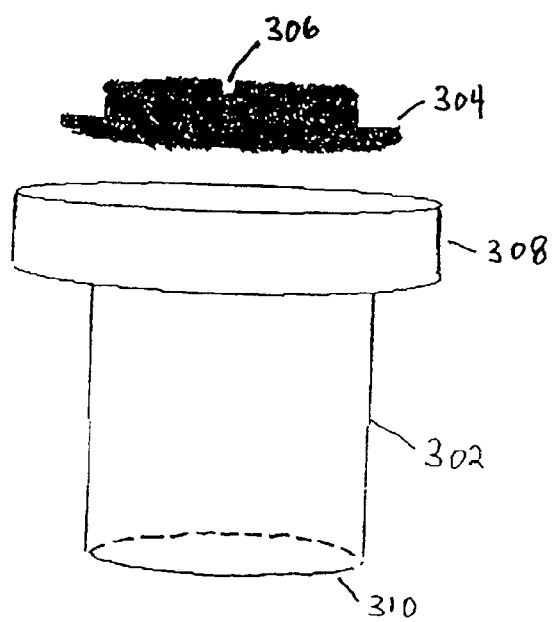
FIG. 3 illustrates a schematic diagram of a effusion cell used as a sample holder.

FIG. 3 shows details of the Knudsen effusion cell. The Knudsen effusion cell comprises: a sample container, 302; an capping plate, 304, with orifice, 306; and, a clamping fixture, 308, which affixes the capping plate to the sample container. The sample container is a cylinder about 4–5 mm in height and about 4–5 mm in diameter and having a disk-shaped bottom portion, 310. The entire structure of cylinder and disk-shaped bottom portion provide a retaining cup for holding a sample which is especially useful for holding liquids. To make a vapor pressure measurement, a sample, e.g. usually a small amount of a liquid organic compound, is placed within the sample container, and the capping plate is crimped into the clamping fixture affixed to the top of the cylinder. The size of the orifice determines the rate of effusion from the Knudsen effusion cell based on formulae known in the art. It is the rate of loss of weight from the effusion cell at a given temperature due to vaporization of the sample in vacuum that is used to determine the vapor pressure of the compound from formulae known in the art.

From FIGS. 2 and 3, it is seen that the thermocouple is not in direct contact with the sample. Consequently, the temperature of the sample within the effusion cell is not accurately measured by the thermocouple. Because of poor thermal conductivity in vacuum, there is a difference between the temperature recorded by the thermocouple and the actual temperature at the sample. In one embodiment of the invention, this difference in temperature is determined by using a slug of ferromagnetic material with a known demagnetization temperature, i.e. Curie temperature, in place of the sample to determine the temperature within the sample container, itself. A magnet is placed beneath the sample holder containing the ferromagnetic slug which causes the balance to register an additional fictitious weight of the slug due to the force exerted by the magnet on the slug. When the temperature of the slug, located at the sample holder, is changed so that the slug loses its magnetization on reaching the Curie temperature, an additional fictitious weight of the slug is lost and a change in the apparent weight of the slug is registered by the instrument. When the magnetic state of the slug changes from a magnetic to a nonmagnetic state, the slug undergoes a magnetic transition that occurs at the Curie temperature. In one embodiment of the invention, the Curie temperatures of each slug in a set of standards is determined. A calibration is obtained of the true temperature within the sample container versus the temperature registered by the thermocouple which reads out on the instrument display of the VTGA, as well as the set-point temperature to which the instrument is set.

One embodiment of the invention is an improved calibration method adapted for calibration of a VTGA at pressures of 5–10 torr, where the low pressures make thermal equilibration within the sample container difficult. Another embodiment of the invention is the use of this improved calibration method to calibrate a VTGA so that the instrument may be used to make highly accurate measurements of the vapor pressures of liquids. The improved calibration method of the present invention overcomes a limitation of previous methods, which depend on one standard or a very limited set of standards that span widely differing Curie temperatures and requires interpolation. The improved method employs a set of temperature calibration standards with a plurality of closely spaced Curie temperatures spanning a lower and more narrow temperature range suitable for measuring the vapor pressure of an organic compound. To measure the vapor pressure of an organic compound, usually requires that the calibration be made at low temperatures, viz. 50 C to 200 C. However, the method can be extended to other materials, e.g. high vapor pressure metals, where a wider range of temperatures is desirable.

Another embodiment of the invention is a set of standards that provides an accurate calibration over a sufficiently numerous set of calibration points within a lower temperature range of interest. This requires a set of standards, each standard with different transition temperatures, Curie temperatures, approximately evenly distributed over the temperature range of interest. In one embodiment, each standard in a set is created by alloying a first ferromagnetic material with another material, either a non-ferromagnetic material, or a second, low Curie temperature ferromagnetic material. Alloys of elemental ferromagnets, such as Fe, Ni, and Co, having relatively high Curie temperatures with Gd having a relatively low Curie temperature provide a suitable set of such standards. For alloys with transition temperatures, i.e. Curie temperatures, or $T_c$'s, from 50 C to 200 C, GdCo alloys with less than 50% Co are candidates for such a set of standards. But, because of their higher cost, lower purity, and difficulty of preparation, Gd-based alloys were found to be less desirable than NiCu alloys.

A set of standards based on NiCu alloys are an embodiment of the invention based on alloying a ferromagnetic material, such as Fe, Ni, Co, and Gd, with another non-ferromagnetic material. Because it was necessary for these NiCu alloys to have compositions providing a range of Curie temperatures spanning the temperature range from 50 C to 200 C, data was sought on the variation of Curie temperature with composition.

Figure 4:
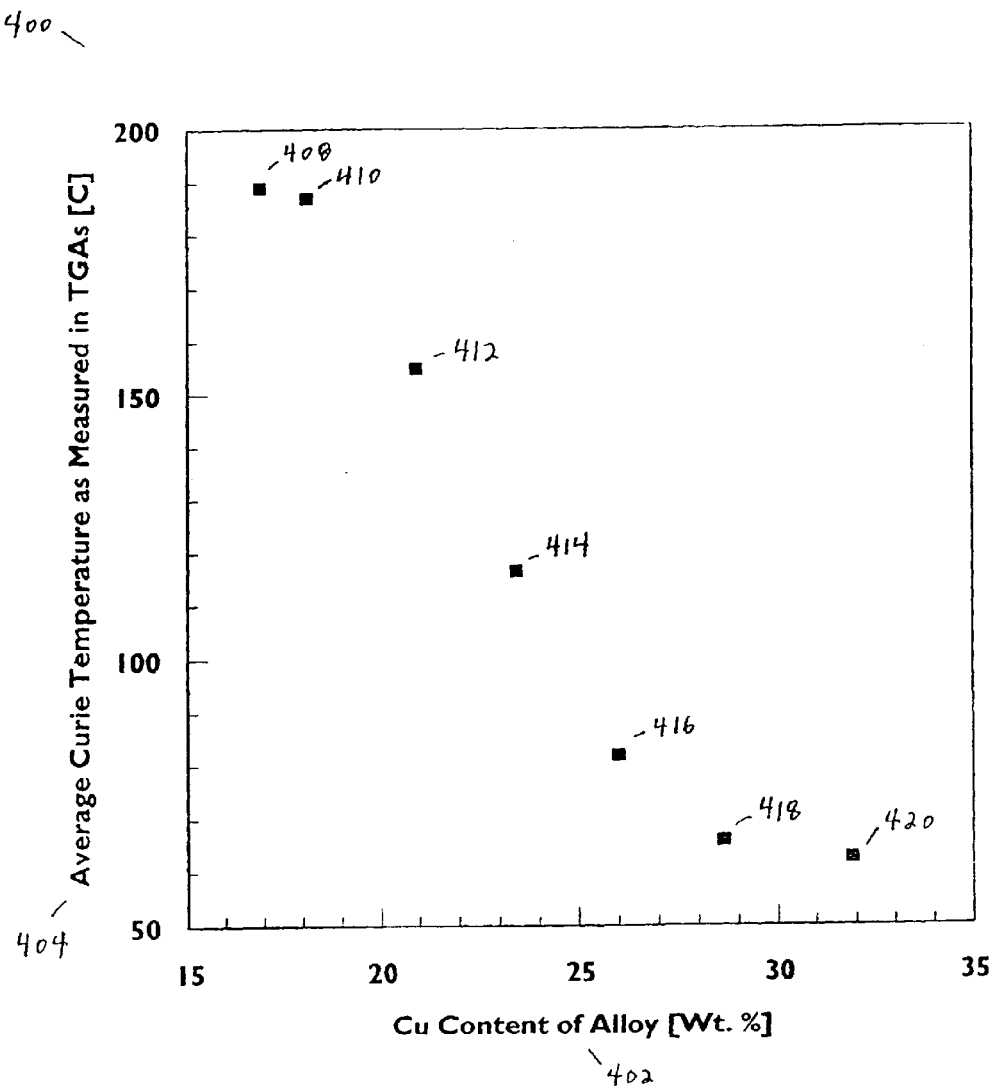
FIG. 4 illustrates a plot showing the dependence of Curie temperature on the composition of ferromagnetic alloys of Cu and Ni used as calibration standards for a VTGA.

FIG. 4 shows the magnetic phase diagram of NiCu alloys made for use as calibration standards. The average Curie temperatures of standards made from slugs of NiCu alloy with varying amounts of Cu are shown, 408 through 420. The values of the average Curie temperatures were obtained by taking the average of the values of the Curie temperature measured for each slug on two different TGA instruments. The composition of various alloys is plotted from its value along the abscissa, 402, in weight % of Cu. The Curie temperature of various alloys is given by its value along the ordinate, 404, in degrees C. As the amount of Cu within the alloy increases, the Curie temperature decreases. A decrease in Curie temperature of a ferromagnetic material with increasing content of non-ferromagnetic constituent is characteristic of a wide variety of ferromagnetic materials composed of a ferromagnetic constituent alloyed with a non-ferromagnetic constituent. Alloys of Ni with Al, Cr, Mo, Ti, W, Mn, Zn or Cu; Co with Cr, or Mo; and Fe with Al, Cr, Ti, Mo or Zn are a but a few examples. However, NiCu alloys with Curie temperatures spanning the range from 50 C to 200 C are particularly well-suited to provide a set of standards over the temperature range of interest for making vapor pressure measurements. A preferred embodiment of the invention relies on these NiCu alloys. Although the use of the magnetic transition of a single NiCu alloy, Monel, to calibrate a TGA is generally known, the use of a set of several such alloys over a limited temperature range for the purpose of calibrating a VTGA to make vapor pressures measurements of a volatile compound through weight loss from an effusion cell is novel. In addition, a set of standards based on magnetic transitions of ferromagnetic alloys is especially useful because the principle disadvantage associated with standards based on the vapor pressure of pure liquid organic compounds, viz. the lack of availability of vapor pressure standards with sufficient purity within a temperature range of interest, is overcome by using solid ferromagnetic alloy standards.

The alloys for the set of standards were prepared by arc melting 99.95% purity Ni and 99.99% purity Cu on a water-cooled copper hearth plate in a reduced pressure atmosphere of high purity Ar. Each alloy was prepared by arc melting two buttons which were subsequently cast together to form a ½ inch diameter rod. Each alloy casting was sealed in a quartz ampoule under inert Ar gas and homogenized annealed at 850 C for 24 hours in a muffle furnace. Following homogenization, the alloy castings were quenched by plunging the ampoule into a water bath while simultaneously breaking the quartz ampoule. Chemical compositions of each alloy were determined by inductively-coupledplasma atomic emission spectroscopy (ICP-AES). The composition of the alloys were from between approximately 17% to 32% Cu by weight, shown in FIG. 4. The Curie temperatures were initially unknown and were determined by TGA measurements, shown in FIG. 4. The alloy rods were cold swaged and drawn into 1.5 mm diameter wires. Small slugs were cut from these wires with a length of, approximately 3 mm. These dimensions of the slugs were chosen so that the slugs could be placed within the sample container of the Knudsen effusion cell of the VTGA for characterization of their thermal magnetic behavior, prior to determination of their Curie temperatures in the TGA, and for later calibration of the VTGA.

Characterization of the thermal magnetic behavior of the slugs near the expected Curie temperatures revealed numerous spurious magnetic transitions obscuring the true determination of the Curie temperatures. These spurious transitions associated with the cold work of the slugs during fabrication were probably due to grain growth and internal defects which were annealing out during the VTGA measurement consequently obscuring the magnetic transition at the Curie temperature. Another embodiment of the invention is an annealing process used to overcome the problem of multiple spurious magnetic transitions. To overcome this problem, the slugs were annealed at 300 C for 1 Hr under 1 Atm $N_2$ gas. Upon recharacterization in the VTGA, the spurious transitions disappeared from the VTGA curves leaving only the transition due to the magnetic transition at the Curie temperature.

Calibration of the VTGA with the slugs as standards requires that the Curie temperatures be accurately determined for each slug. To determine the Curie temperatures of each slug, their transition temperatures, i.e. Curie temperatures or points, $T_c$'s, were measured at atmospheric pressure twice in two separate well-calibrated TGAs. The results of these measurements are shown in FIG. 4. Since convection currents within the TGA instrument at atmospheric pressure made is easier to efficiently establish thermal equilibrium between the test cell and the slug, measurements made in the TGAs at atmospheric pressure assured accurate measurements of the Curie temperatures. The linearity of the TGA systems over the temperature range of interest had been previously established in prior use. Thus, a complete set of VTGA calibration standards with well characterized Curie temperatures, was obtained spanning the temperature range between approximately 50 C and 200 C. The accuracy of the determination of the Curie temperatures of the standards was confirmed by verifying the Curie temperature of a certified magnetic reference standard Alumel ($T_c$_149 C) on both systems used to obtain the Curie temperatures for the NiCu slug standards.

Another embodiment of the invention is a method of using a set of calibration standards comprised of a plurality of ferromagnetic slugs to provide a temperature calibration for a VTGA. Since the heat transfer to the sample in vacuum is limited by radiative transfer, there are significant differences between the temperature on the VTGA controller display provided by the thermocouple, the VTGA set point, and the temperature at the sample. Therefore, after a slug whose Curie temperature had been measured in a TGA was placed in the sample holder of the VTGA, the VTGA was allowed to equilibrate at an initially higher temperature (typically 10 degrees above $T_c$ found in the TGA), where it was held isothermally for 1 hour, subsequently, the temperature was increased by heating at a rate of 5 degrees/min to a temperature 2 degrees higher than the initial temperature, where once again it was held isothermally for 2 hours. The second step was repealed at successively higher temperatures, approximately 10 times, until $T_c$ was detected in the VTGA. To confirm the detected $T_c$, a second isothermal holding experiment was then performed for a time interval of about 320 minutes at the temperature at which $T_c$ was previously detected.

Figure 5:
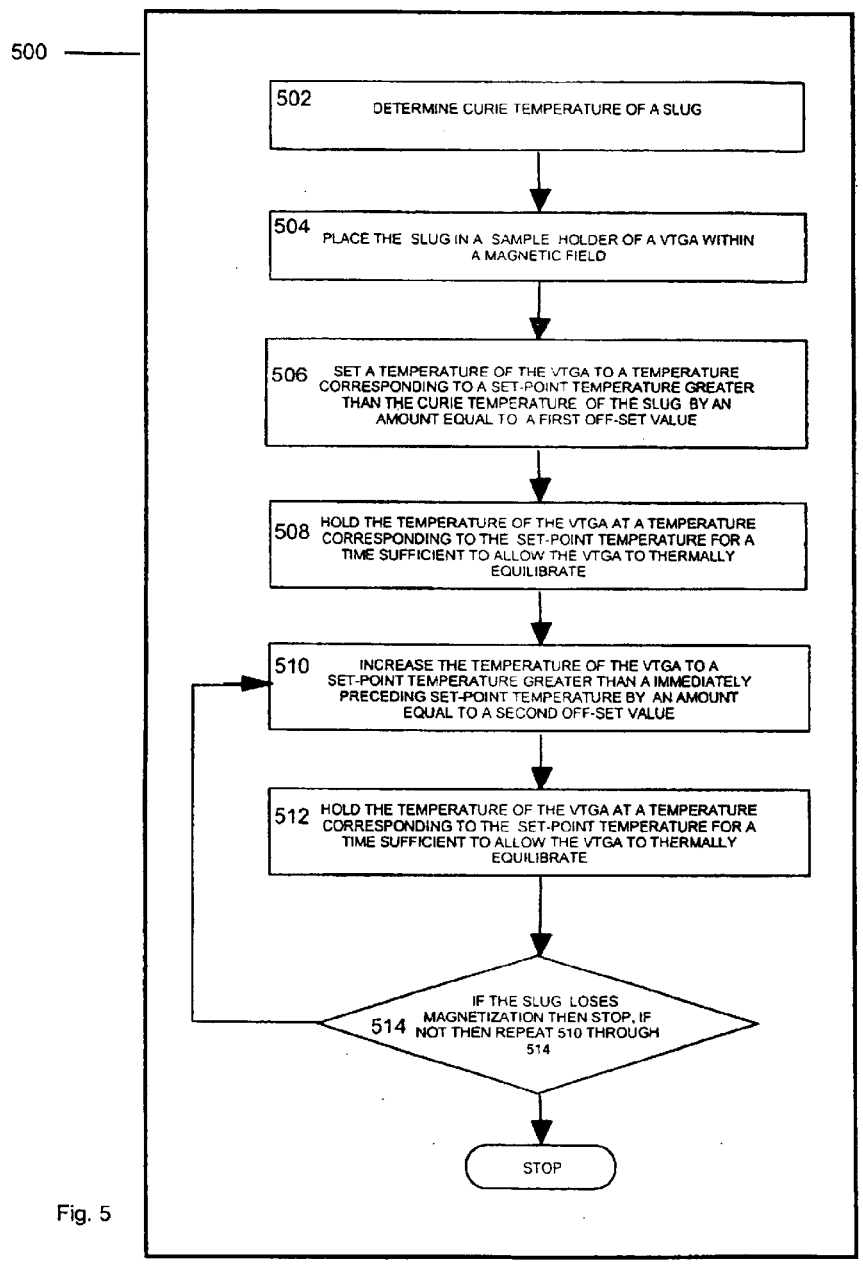
FIG. 5 illustrates a flow chart of a method of calibrating a VTGA using a set of calibration standard slugs; and, FIG. 6 illustrates a calibration curve used to calibrate a VTGA comparing "True" Curie temperatures of the calibration standards measured in a TGA versus "Apparent" Curie temperatures indicated by the set-point temperature of a VTGA.

FIG. 5 is a flow chart that illustrates an embodiment of the invention, a method of using a set of calibration standards comprised of a plurality of ferromagnetic slugs to provide a temperature calibration for a VTGA. First, the Curie temperature of each slug is determined. A previously well-calibrated TGA was used to determine the Curie temperatures of each slug in a TGA. 502, by methods known to those skilled in the art. However, other known methods of determining the Curie temperature could be used, such as magnetometer measurements at controlled temperatures. Next, the temperatures at which each slug lost magnetization, i.e. underwent a magnetic transition were determined in the VTGA. This gave an apparent Curie temperature for the VTGA at which the transition occurred for each slug. These Curie temperatures were determined as follows: place the slug in a sample holder of a VTGA within a magnetic field, 504; set a temperature of the VTGA to a temperature corresponding to a set-point temperature greater than the Curie temperature of the slug by an amount equal to a first offset value, 506; hold the temperature of the VTGA at a temperature corresponding to a set-point temperature for a first time interval sufficient to allow the VTGA to thermally equilibrate, 508; increase the temperature of the VTGA to a set-point temperature greater than an immediately preceding set-point by an amount equal to a second offset value, 510; hold the temperature of the VTGA at a temperature corresponding to a set-point temperature for a second time interval sufficient to allow the VTGA to thermally equilibrate, 512; and, if the slug does not lose magnetization, then repeat the previous two operations, and afterwards return to this test; but if not, then record the set-point temperature at which the slug loses magnetization as the apparent Curie temperature of the slug, 514. This procedure is repeated for each slug until the apparent Curie temperatures of all slugs has been determined.

Figure 6:
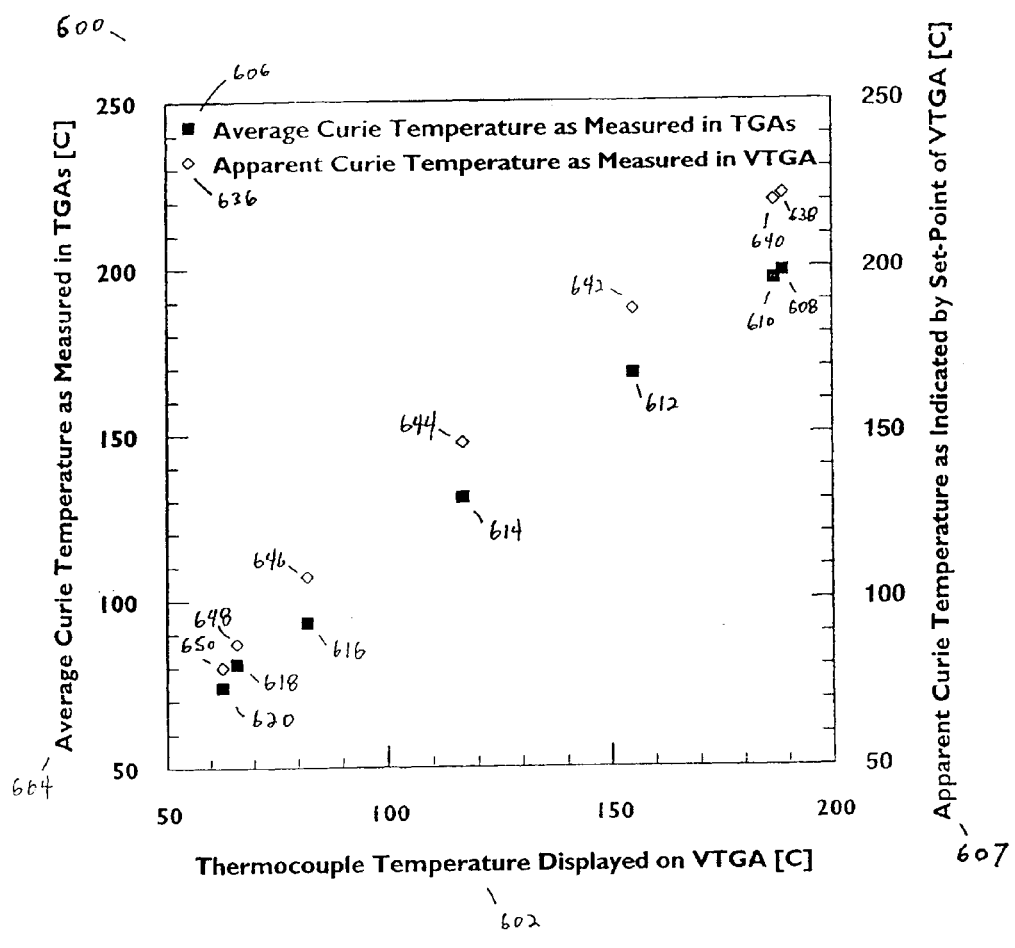

The results 600 of the calibration of the VTGA are presented in FIG. 6. The values, 608 through 620, of the average Curie temperatures of the set of standards as measured in the TGAs at ambient atmospheric pressure are shown thereon as closed squares, 606. The values, 638 through 650, of the apparent Curie temperatures of the set of standards as measured in VTGA in vacuum at about $10^{-5}$ Torr pressure are shown thereon as open diamonds, 636. These values are plotted as a function of the thermocouple temperature displayed on the VTGA, 602, given by the abscissa. Dual axes with the same scales are used to plot these values. The first ordinate gives the values for the average Curie temperatures of the standards as measured in the TGAs, 604. The second ordinate gives the values for the apparent Curie temperatures of the standards as set by the set-point temperature of the VTGA, 607. In order to produce a magnetic transition in a given slug from the set of standards, it is necessary to set the set-point of the VTGA to a temperature higher than the Curie temperature, $T_c$, measured in the TGAs. The temperature measured by the thermocouple and displayed by the TGA controller is always lower than both the actual Curie temperature, $T_c$, and the set-point temperature. The graph portrays the differences between the values of the "true" Curie temperature, given by the average of the Curie temperatures as measured in the TGAs, and the "apparent" Curie temperature, given by the set-point temperature, which are shown in FIG. 6 as the vertical deviations between the data points: 638 and 608, 640 and 610, 642 and 612, 644 and 614, 646 and 616, 648 and 618, and 650 and 620, for a given displayed VTGA controller temperature. The deviation between these values gives the calibration of the instrument. It tells the operator what the actual temperature is within the sample holder for a given set-point temperature set by the operator of the instrument. In this case, the calibration is given versus the set-point temperature rather than the temperature measured at the thermocouple displayed by the VTGA, because the operator has direct control over the set-point temperature of the system, whereas control over the thermocouple temperature is a passive result of what the set-point temperature is set at.

Advantages and utility of embodiments of the present invention include calibrating at the location of the sample on the sample holder, and eliminating innumerable sources of error in the calibration. Note that errors in the temperature of only 10 degrees can lead to large errors in the determination of a vapor pressure measurement. Thus, embodiments of the invention have utility for establishing the amounts of costly lubricants, and rust inhibitors, as well as other chemical constituents to be placed in disk drives.

Although specific embodiments of the invention have been described and illustrated, one skilled in the art will recognize other embodiments, not expressly described, but which fall within the scope of the invention.

What is claimed is:

1. A method to provide a temperature calibration for a vacuum thermogravimetric analyzer (VTGA) comprising:

selecting a plurality of ferromagnetic slugs wherein each slug includes an alloy including nickel and copper and wherein the amount of cooper is within the range of 15% to 28%;

determining the Curie temperature of a each slug;

placing each slug in a sample holder of a VTGA within a magnetic field;

setting a temperature of the VTGA to a temperature corresponding to a first set-point temperature greater than the Curie temperature of each slug by an amount equal to a first offset value;

holding the temperature of the VTGA at a temperature corresponding to a said first set-point temperature for a first time interval sufficient to allow the VTGA to thermally equilibrate;

increasing the temperature of the VTGA to a second set-point temperature greater than an immediately preceding set-point by an amount equal to a second offset value;

holding the temperature of the VTGA at a temperature corresponding to a said set-point temperature for a second time interval sufficient to allow the VTGA to thermally equilibrate; and, if each slug does not lose magnetization, then repeating the previous two operations, afterwards returning to this test; but if not, then recording the set-point temperature at which each slug loses magnetization as the apparent Curie temperature of each slug.

\* \* \* \* \*

UNITED STATES PATENT AND TRADEMARK OFFICE
CERTIFICATE OF CORRECTION

PATENT NO.        : 6,871,998 B2                                           Page 1 of 1
APPLICATION NO. : 10/632507
DATED             : March 29, 2005
INVENTOR(S)       : Carter et al.

It is certified that error appears in the above-identified patent and that said Letters Patent is hereby corrected as shown below:

column 10, line 24: after the word "of" and before the word "each" please remove the word "a"

column 10, line 32: after the word "to" and before the word "said" please remove the word "a"

column 10, line 40: after the word "to" and before the word "said" please remove the word "a"

Signed and Sealed this

Second Day of September, 2008

JON W. DUDAS
*Director of the United States Patent and Trademark Office*